(12) United States Patent
Leandersson et al.

(10) Patent No.: US 6,382,833 B2
(45) Date of Patent: May 7, 2002

(54) X-RAY EXAMINATION APPARATUS

(75) Inventors: Enar Leandersson, Ekerö; Arne Borggren; Jan Narfström, both of Sollentuna, all of (SE)

(73) Assignee: Siemens-Elema AB, Solna (SE)

( * ) Notice: Subject to any disclaimer, the term of this patent is extended or adjusted under 35 U.S.C. 154(b) by 0 days.

(21) Appl. No.: 09/736,311

(22) Filed: Dec. 15, 2000

(30) Foreign Application Priority Data

Dec. 17, 1999 (SE) .............................................. 9904644

(51) Int. Cl.[7] .................................................. H05G 1/02
(52) U.S. Cl. ...................................... 378/197; 378/196
(58) Field of Search ................................. 378/185, 196, 378/197, 193

(56) References Cited

U.S. PATENT DOCUMENTS

| | | | |
|---|---|---|---|
| 4,879,737 A | 11/1989 | Grady | 378/196 |
| 4,922,512 A | * 5/1990 | Lajus et al. | 378/197 |
| 5,155,757 A | * 10/1992 | Sakaniwa et al. | 378/197 |
| 5,367,554 A | * 11/1994 | Kobayashi et al. | 378/196 |
| 5,479,470 A | 12/1995 | Stenfors | 378/196 |
| 6,315,446 B1 | * 11/2001 | Kidd et al. | 378/197 |

FOREIGN PATENT DOCUMENTS

| | | |
|---|---|---|
| JP | 8-71062 | 3/1996 |
| WO | WO 99/17659 | 12/1999 |

\* cited by examiner

*Primary Examiner*—Drew Dunn
(74) *Attorney, Agent, or Firm*—Schiff Hardin & Waite

(57) ABSTRACT

An X-ray examination apparatus has a base and a support connected by an arm arrangement. The support is connected to a holding device in which a curved carrier is displaceably mounted, the curved carrier having an X-ray emitter at one end and a radiation detector at an opposite end. An examination table is movable between the X-ray emitter and the radiation detector. The arm arrangement is composed of at least first and second arms. The first arm is rotatably mounted at a shaft at the base, and the second arm is rotatably mounted at a shaft at the carrier. The respective free ends of the first and second arms are rotatably connected to each other by another shaft. The carrier, without bothersome components of the stand beneath the examination table, can be rotated 90° from a head-adjusted position in both directions to lateral positions, while maintaining the isocenter at a fixed position, and the carrier also can be lowered to the floor on which the base is disposed. For this purpose, the first and second arms are disposed in different planes and have respective lengths, dependent on the position of the shaft at the base and the distance between the shaft of the support and the central beam of the X-ray emitter, so that the curved carrier, by means of the arms, can be rotated around an intersecting point formed by the central beam of the X-ray emitter cutting the center line of the examination table, with a centrally head-adjusted stand.

3 Claims, 3 Drawing Sheets

X-RAY EXAMINATION APPARATUS

BACKGROUND OF THE INVENTION

1. Field of the Invention

The invention relates to an X-ray examination apparatus of the type having a stand with a base, an arm arrangement with a first end mounted for rotation around a first vertical shaft that is attached to the base and with a second end that carries a support, which is mounted for rotation around a second vertical shaft, whereby the support is connected to a holding device, with a curved carrier displaceably arranged therein, with an X-ray tube and a radiation receiver mounted opposite each other at opposite ends of the carrier, and with an examination table.

2. Description of the Prior Art

In connection with X-ray examinations with an apparatus of the aforementioned known type, an examination table is utilized, which can be displaced at least along its longitudinal direction It is of great advantage with respect to a heart examination, for example, when the curved carrier of the stand can be moved from a head-adjusted position, in which the stand and the carrier are arranged behind the top end of the examination table and in which the top end is placed between the X-ray tube and the radiation detector, into a lateral position, in which the carrier, in a vertical position, is perpendicularly arranged relative to the fictive center axis of the examination table, while the isocenter stays in the same location in space. It is also of great advantage when the carrier can be rotated 180° from the described lateral position into a mirror-inverted lateral position at the other side of the table, also while the isocenter stays fixed. Thus, the physician's team has wide-ranging access to the patient.

U.S. Pat. No. 4,922,512 describes an X-ray examination stand of the aforementioned type. The base, around whose shaft the arm and the support are rotatably connected, is attached to the floor below the top end of the examination table. Due to the arm extending under the table and due to the vertical shaft of the base being in axial alignment with a center line between the X-ray tube and the receptor, the stand with the carrier for the X-ray tube and the detector can be rotated from a centrally head-adjusted position into a position, in which the carrier is arranged at an angle of 90° in relationship to the longitudinal direction of the table without changing the position of the isocenter. Proceeding from this described position, the stand and the carrier always can be rotated by 180° into a corresponding position at the other side of the examination table, again without changing the position of the isocenter. Since the arm at the floor is relatively large and high in the region of the axis of the fastening device, the physician might push against the floor arm with his for her feet during an examination, which can be bothersome. Due to the position and vertical height of the arm, the carrier for the X-ray tube and the detector cannot be lowered completely to the floor given a vertical position of the carrier. In such a vertical position, it would be desirable in a few cases to be able to lower the X-ray tube and the detector by another 4 to 5 cm, so that a good working height is provided for the physician, but this approximately corresponds to the vertical height of the arm. This is a limitation of the adjustment possibilities of the X-ray tube and the detector. Besides, the floor arm and the base restrict the access to the patient.

SUMMARY OF THE INVENTION

An object of the present invention is to provide an X-ray examination apparatus with a stand of the aforementioned type, which is relatively simple and compact in its structure and which, in connection with an examination table, the carrier, without disturbing stand parts under the table, can be rotated 90° in both directions from a head-adjusted position into vertical lateral positions without changing the position of the isocenter. Another object is to provide such an apparatus which allows the carrier for the stand to be lowered to the floor.

This object is inventively achieved in an X-ray examination apparatus of the type described above wherein the arm arrangement is composed of at least two arms, which are mounted in different planes, with the respective free ends of these arms being rotatably connected to one another around a vertical shaft, and wherein the respective lengths of the arms, depending on the position of the vertical shaft at the base and on the distance of the rotational axis of the support from the central beam for the X-ray tube and the detector, are dimensioned such that the curved carrier, by means of the arms, can be rotated around an intersecting point, which is formed by the central beam cutting the center line of the examination table with respect to the centrally head-adjusted stand. A stand that is simple and compact regarding its structure is achieved due to the fashioning of the arm arrangement and due to the lengths of the arms, whereby the carrier of the stand can be rotated 90°, with a fixed-position isocenter, from a head-adjusted position into a laterally positioned vertical position at the one side of the examination table, or can be rotated 90° into a laterally positioned vertical position at the other side of the examination table. Disturbing parts under the table are avoided by the described structure of the stand. The physician's team can now choose from which side they wish to most easily access the patient.

In an embodiment, the arms are disposed above one another given a centrally head-adjusted stand position. A relatively compact stand results.

The fastening point for the base is inventively placed such that the curved carrier does not touch the base in any position that can be reached by rotation around the intersecting point. It is thereby achieved that the curved carrier can be lowered to the floor.

The brochure "ARCOSKOP" of Siemens AG shows a ceiling mount with an arm arrangement, having one end that can be rotated around a vertical shaft that is attached to the base and having an opposite end that carries a support The support is connected to a holding device for a curved carrier, which carries an X-ray tube and a detector. Although the arm arrangement is composed of two arms arranged in different planes, the lengths of the arms are not dimensioned such that the carrier can be partially rotated into a lateral vertical position at the one side of the table and partially into a lateral vertical position at the other side of the table given a centrally head-adjusted stand with a fixed-position isocenter.

DESCRIPTION OF THE PREFERRED EMBODIMENTS

Figure 1:
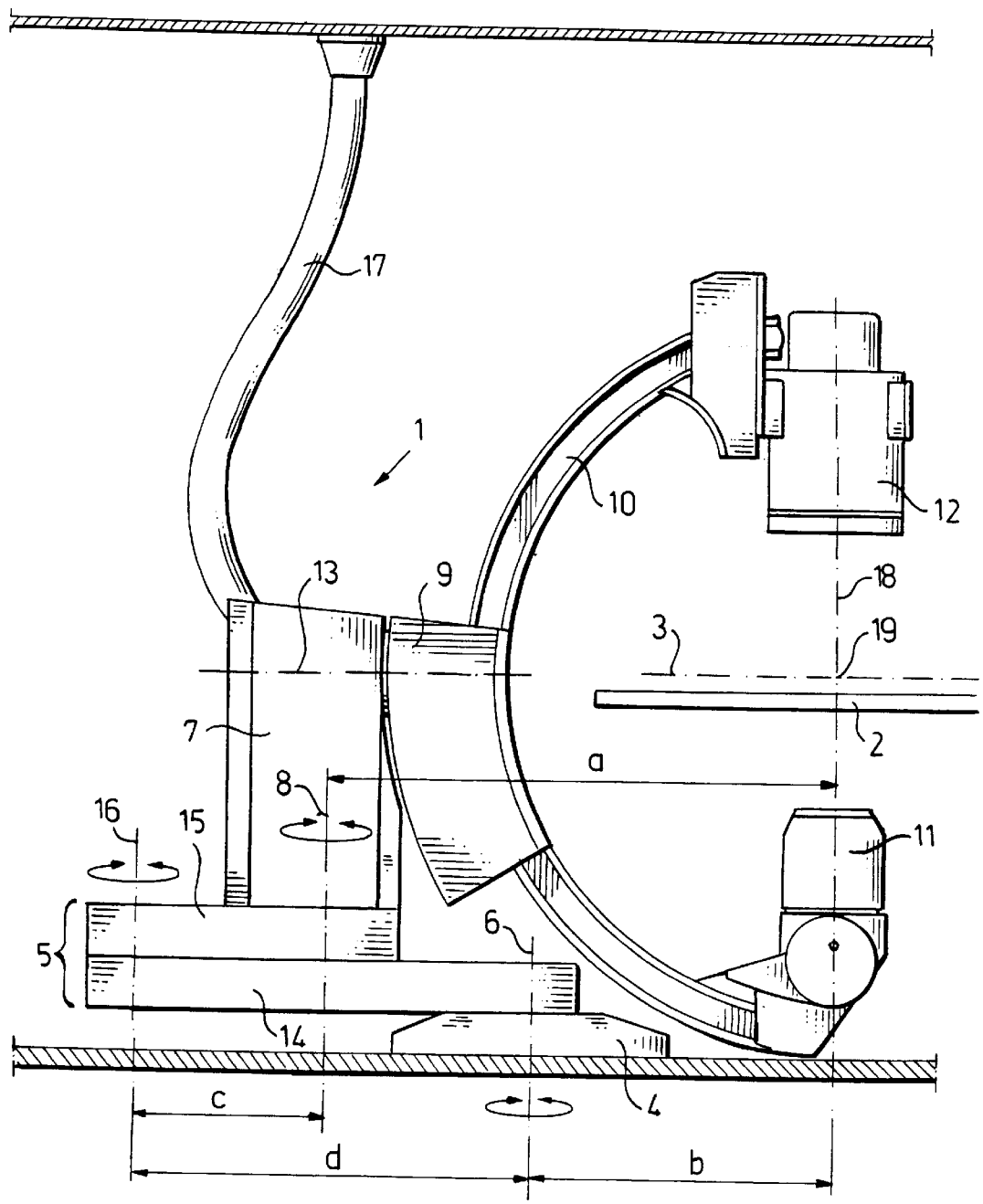
FIG. 1 is a side view of an X-ray examination apparatus in accordance with the invention.

FIG. 1 shows an X-ray examination apparatus having a stand 1 that is fixed to the floor and shows a part of the examination table 2, which can be displaced, preferably in its longitudinal direction along a center axis 3. The stand 1 has a base 4 with an arm arrangement 5, with one end that can be rotated around a vertical shaft 6 that is arranged in the base 4. The other end of the arm arrangement 5 carries a support 7, which is mounted for rotation around a vertical shaft 8. The support 7 is connected to a holding device 9 in which a curved carrier 10 is displaceably mounted. One end of the carrier 10 carries an X-ray tube 11 and its other end carries a radiation detector 12, which are oriented opposite to one another. The holding device 9, in turn, is connected to the support 7 so as to be rotatable around a shaft 13. The arm arrangement 5 is composed of two arms 14, 15, which are arranged in different planes, and whose respective free ends are rotatably connected to one another around a vertical shaft 16. FIG. 1 also shows a central cable 17 for the electrical supply of the stand 1. FIG. 1 shows the stand in a centrally head-adjusted position. In such a position, the arms 14, 15 are situated above one another.

Depending on the position of the vertical shaft 6 in the base 4 and on the distance between the swivel shaft 8 of the support 7 and the central beam 18 of the X-ray tube 11 and the detector 12, the lengths of the arms 14, 15 are dimensioned such that the support 10 can be rotated with the arms 14, 15, by means of drive devices that are described later, around an intersecting point 19 (isocenter), which is formed by the central beam 18 cutting the center line 3 of the examination table with a centrally head-adjusted stand 1. The distance between the shaft 8 and the shaft 16 of the arm 15, which is referred to as c in FIG. 1, and the distance between the shaft 15 and the shaft 6 for the arm 14, which is referred to as d, is determined by the following relationship:

$$a+c=b+d,$$

whereby a is the distance between the central beam 18 and the shaft 8, and b is the distance between the central beam 18 and the shaft 6. The distance b is preferably dimensioned such that the carrier 10 is neither touched by the base 4 nor by the arm given a head-adjusted position. This contributes to the compact structure of the stand.

Figure 2:
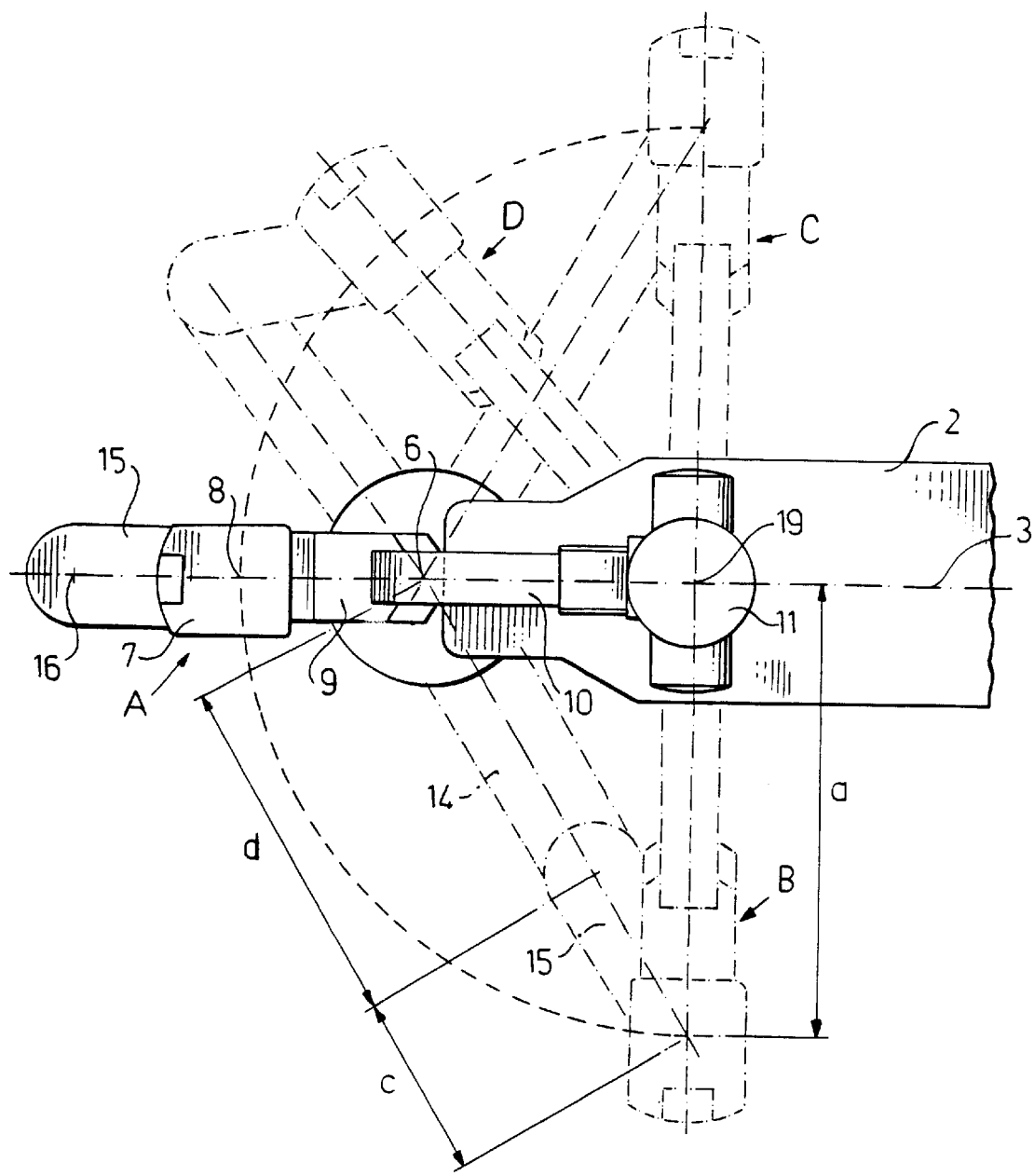
FIG. 2 is a plan view of the stand according to FIG. 1 in different positions.

In FIG. 2, which is a plan view of the X-ray examination apparatus of FIG. 1, the stand 1 is shown in a centrally head-adjusted position A. The carrier 10 for the X-ray tube 11 and the receptor 12, with the aid of a drive device (explained below), can now be rotated, as already mentioned, with a fixed-position isocenter from the centrally head-adjusted position A 90° into a lateral vertical position B at the one side of the examination table 2 or into a lateral vertical position C at the other side of the examination table 2. In this lateral vertical position, the distance between the shaft 6 and the shaft 8 equals c+d. FIG. 2 also shows an arbitrary position D between the positions A and C. An X-ray examination also can be carried out in such an intermediate position. Since the carrier 10 of the stand 1 can be rotated in the described way, the physician's team has particularly easily access to the patient (not shown) situated on the examination table 2— regardless of the side of the examination table 2 from which they wish to work.

The figures show that the base 4 is placed such that the curved carrier 10 does not touch the base in any position that can be reached during a rotation around the intersecting point 19. As a result, the carrier 10 can be lowered to the floor (as shown in FIG. 1).

The drive device for the arms 14, 15 and for the support can be formed by wheels, which are attached to the shafts 6, 8, 16, connected by the chains or belts in a known way, with at least one wheel being driven by a motor. The chain or belt drive has a transmission ratio, which, with the aid of the motor, now forces the carrier 10 to rotate around the aforementioned isocenter. Respective motors that are connected to the shafts 6, 8, 16 also can be utilized as drive devices. Preferably, the motors are software-controlled. Drive devices of this type are known and therefore need not be shown or explained in greater detail herein.

Figure 3:
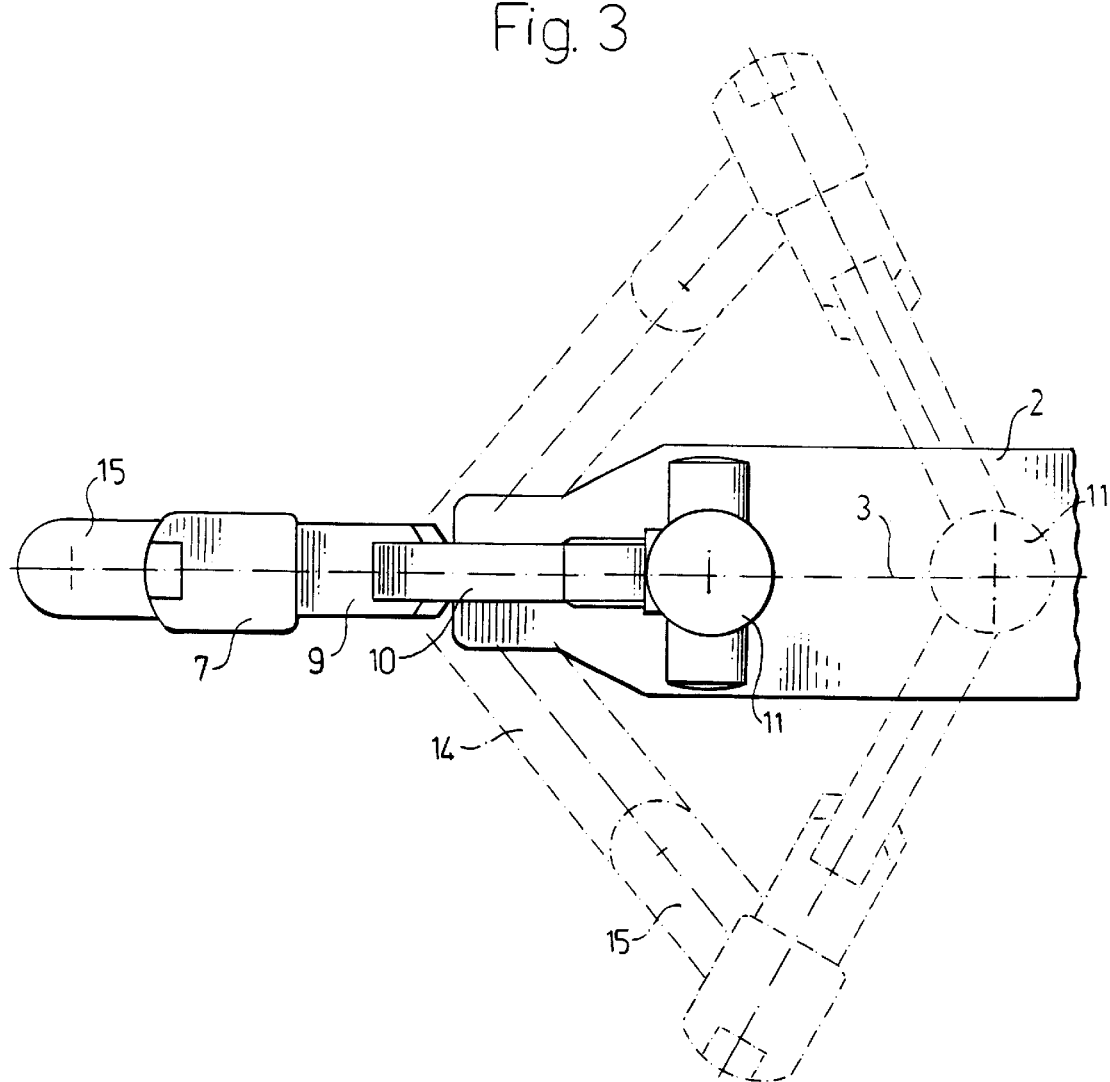
FIG. 3 is a plan view of the stand of FIG. 1 displaced into further positions.

FIG. 3 shows that the stand 1 also can be displaced such that the central beam 18 for the X-ray tube. 11 and the detector 12 can be displaced along the center line 3 of the examination table. Such a displacement of the stand 1 can ensue from both longitudinal sides of the table 2. In association therewith, a drive device of the aforementioned type, which is composed of motors, is preferably used.

The inventive stand can also be a ceiling mount when the support 7 is extended.

Although modifications and changes may be suggested by those skilled in the art, it is the intention of the inventors to embody within the patent warranted hereon all changes and modifications as reasonably and properly come within the scope of their contribution to the art.

We claim as our invention:

1. An X-ray examination apparatus comprising:

a base having a first vertical shaft and a second vertical shaft;

a curved carrier having first and second opposite ends;

an X-ray emitter mounted at said first end of said carrier and a radiation receiver mounted at said second end of said carrier disposed opposite said X-ray emitter, said X-ray emitter emitting a central X-ray beam;

an examination table movable between said X-ray emitter and said detector; and an arm arrangement connected between said first shaft and said second shaft, said arm arrangement comprising a first arm rotatably mounted at said first shaft and having a first arm free end, and a second arm rotatably mounted at said second shaft and having a second arm free end, said first arm free end and said second arm free end being rotatably connected around a third vertical shaft, and said first and second arms having respective lengths so that, dependent on a position of said first shaft at said base and a distance between said second shaft and said central beam said carrier is rotatable by said first and second arms around an intersecting point formed by said central beam cutting a center line of said examination table with said X-ray emitter and said radiation detector disposed on opposite sides of said examination table and said central beam proceeding vertically through said examination table.

2. An X-ray examination apparatus as claimed in claim 1 wherein said first arm and said second arm are disposed above one another when said carrier is disposed with said X-ray emitter and said radiation detector on opposite sides of said examination table and said central beam proceeding vertically through said examination table.

3. An X-ray apparatus as claimed in claim 2 wherein said base is disposed so that said carrier is out of contact with said base for all rotational positions of said carrier.

* * * * *